United States Patent
Regester et al.

[19]

[11] Patent Number: 6,109,139
[45] Date of Patent: Aug. 29, 2000

[54] CAP REMOVING TOOL

[75] Inventors: David J. Regester, West Grove, Pa.; W. Mark Barbour, Newark, Del.

[73] Assignee: Qualicon, Wilmington, Del.

[21] Appl. No.: 09/074,499

[22] Filed: May 8, 1998

[51] Int. Cl.[7] ...................................................... B67B 7/04
[52] U.S. Cl. ................ 81/3.47; 81/3.55; 81/3.09
[58] Field of Search ................... 81/3.09, 3.55, 81/3.47, 3.56, 3.48

[56] References Cited

U.S. PATENT DOCUMENTS

| | | | |
|---|---|---|---|
| 1,707,398 | 4/1929 | Hyland | 81/3.09 |
| 1,810,795 | 6/1931 | Soderquist | 81/3.48 |
| 3,043,171 | 7/1962 | Lederer | 81/3.48 |
| 3,256,756 | 6/1966 | Del Piccolo | 81/3.48 |
| 3,787,946 | 1/1974 | Schimek | 81/3.47 |

OTHER PUBLICATIONS

MicroAmp® Cap Installing Tool, *Perkin Elmer 1996–1997 Catalogue*, p. 59.

Cap–It, *Advanced Biotechnology 1997/98 Catalogue*, p. 31.

*Primary Examiner*—David A. Scherbel
*Assistant Examiner*—Joni B. Dangaman

[57] ABSTRACT

A tool for use in removing a plurality of spaced apart caps while said caps are in locked engagement with a plurality of corresponding tubes comprises a body have a first portion adapted to be engaged by the user and a second portion having a plurality of spaced apart pegs extending from the body, the pegs being of such size, shape and relative spacing as to be closely received within a corresponding hollow in the cap, whereby, upon insertion of the pegs into the caps and application of a rocking force to the tool, the tubes are uncapped nearly simultaneously.

6 Claims, 2 Drawing Sheets

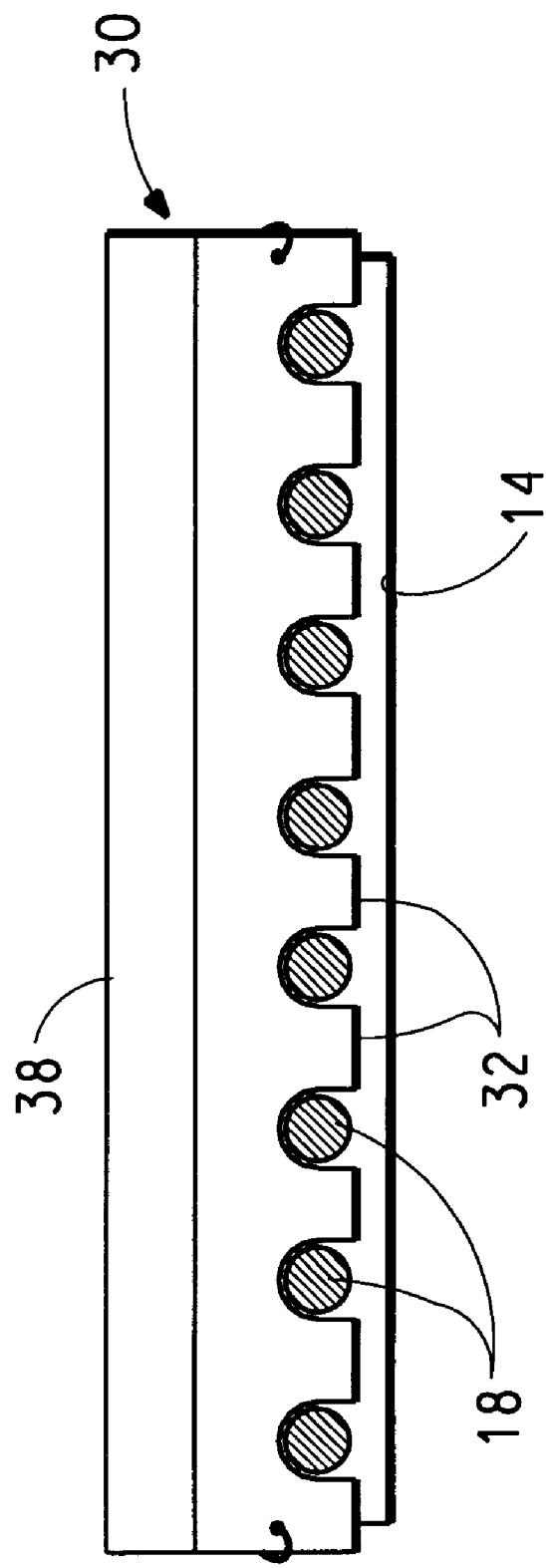

CAP REMOVING TOOL

BACKGROUND OF THE INVENTION

This invention relates to the field of laboratory apparatus, particularly apparatus used for performing polymerase chain reaction ("PCR") and similar types of processes. Still more particularly, the invention relates to a tool for removing and installing caps of reaction tubes used in such processes.

PCR is a widely used procedure in which a small amount of DNA is amplified (i.e., reproduced) to yield a higher concentration of the DNA for further study, testing, etc. See U.S. Pat. No. 4,683,195 and U.S. Pat. No. 4,683,202. The steps of the reaction require the samples to undergo a series of thermal treatments wherein the samples are repeatedly cycled between two temperatures, such as between 70° C. and 94° C. about 35 times. It has become common to perform PCR, as well as a number of other processes, in reaction tubes. The reaction tubes are small plastic containers (each holding approximately 0.2 $\mu$l) having a generally cylindrical shape with a conical bottom and a removable cap at the top. Because of their small size, the tubes are commonly sold connected together in strips of 8 or 12 tubes. An equal number of caps is provided as a matching strip. A strip of caps has tabs at each end to facilitate removal of the strip.

Twelve strips of 8 tubes ordinarily are loaded into wells in a tube rack for processing. In some apparatus, four such tube racks are processed simultaneously. In use, the operator loads a strip of capped tubes into the tube rack and removes the strip of caps by pulling on the tab to lift the caps progressively from one end to the other. The tubes are then loaded with the appropriate reagents, usually with a micropipette and recapped by hand. The procedure of uncapping and recapping is repeated after the PCR or other process to remove the samples for analysis.

If the tubes are empty, the act of removing the strip of caps in rapid succession obviously does not present any problem of ejecting the contents. However, when necessary to uncap the tubes when they are full or partially full (as in the case of tubes purchased pre-packaged with reagents), it is often the case that some of the contents will be released. It is even sometimes the case that recapping the tubes might result in spillage of some of the contents. To minimize spillage, the technician will typically need to carefully remove and/or replace one cap at a time, which is not only tedious and time consuming, but also requires repetitive movements. Also, spillage of DNA material is highly undesirable because of the potential for contamination of adjacent and subsequent reactions. Moreover, practice has shown that the closely packed tubes in the tube rack are difficult to recap. A careless or hurried technician may not always get all tubes properly recapped all of the time which can result in test failures due to evaporation during heating. Even when the tubes are uncapped while empty, removing strips of caps by hand often results in stretching of the strip making recapping difficult and subject to failure.

In addition to the common reaction tubes described above, which have a dome-shaped cap that projects above the top of the tube when seated, there is another, larger tube commonly used in the PCR and other laboratory processes. This tube holds about 1.2 ml and is typically used for lysis or incubation reactions. These tubes are equipped with a concave, bowl-shaped cap which projects into the interior of the tube when seated. Such caps are commercially available as "GeneMate®" caps T-3122-4 from Intermountain Scientific Corporation BioExpress. Co-pending U.S. patent application Ser. No. 09/013,315, filed Jan. 26, 1998 discloses and claims a tool for removing the dome-shaped caps. The present invention, however, is particularly designed for removal of the concave caps.

SUMMARY OF THE INVENTION

It is, therefore, an object of this invention to provide a tool for easy uncapping and/or recapping of strips of reaction/processing tubes and the like without disturbance of the contents thereof.

In one aspect, the invention provides a tool for use in uncapping a plurality of linearly-oriented, spaced-apart tubes, the tool comprising:

a) a body having a first portion for engagement by a user and a second portion adapted to engage a plurality of caps while said caps are in locked engagement with a plurality of corresponding tubes;

b) said second portion comprising a row of spaced-apart pegs projecting from said body, said pegs being of such size, shape and position to be closely received within a corresponding hollow in a cap.

In a particularly preferred embodiment, the tool further includes a device for disengaging the strip of caps from the plurality of pegs.

These and other aspects of the invention will become apparent upon a further reading of the specification with reference to the drawings and the appended claims. The invention is described and illustrated with particular reference to its use in uncapping PCR tubes and the like. It is to be understood, however, that the invention is not intended to be limited to that particular use and that the invention may be equally useful to uncap any small container having a concave cap structure.

BRIEF DESCRIPTION OF THE DRAWINGS

FIG. 3 is a bottom plan view, partly in section, of the tool as seen along lines and arrows 3—3 of FIG. 2, particularly illustrating the cap removal feature of the preferred embodiment.

DETAILED DESCRIPTION OF THE INVENTION

Figure 1:
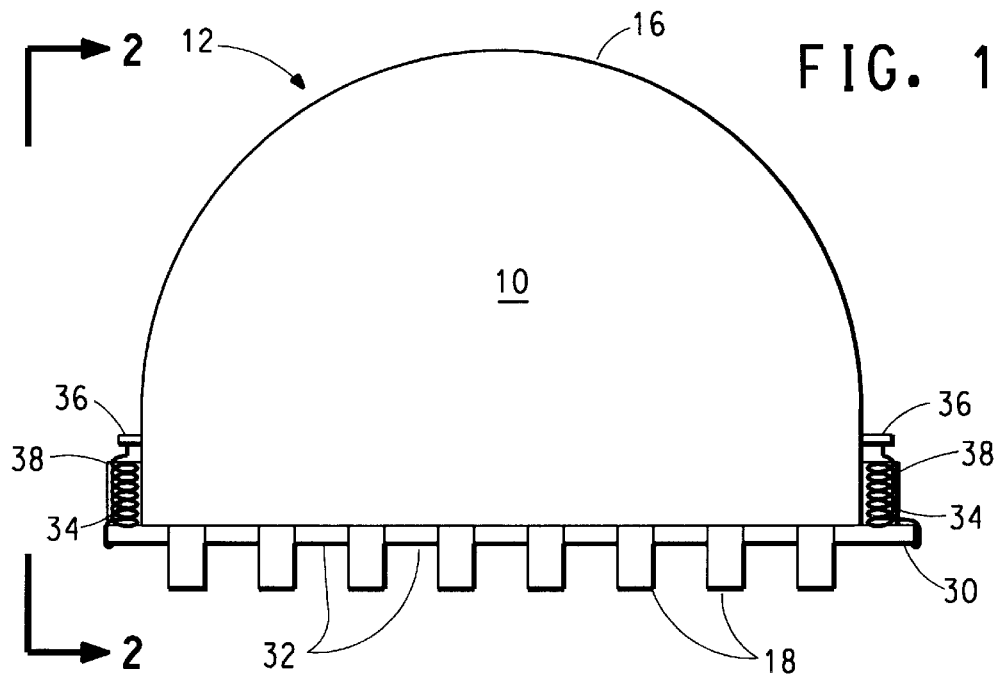
FIG. 1 is a front elevation view of a preferred embodiment of the tool of the invention.

With reference first being made to FIG. 1, a preferred embodiment of the tool of the invention is illustrated therein. As seen in FIG. 1, the tool comprises a body 10 having a first portion 12 adapted for engagement by a user and a second portion 14 adapted to engage a plurality of caps.

In the embodiment illustrated, the body 10 has a generally smooth, semi-circular configuration. It is understood that the precise configuration of the body 10 is not critical to the invention and that the shape is more a matter of intended end use, user convenience or ergonomic and aesthetic considerations. The shape of the tool shown was selected for ergonomic reasons and incorporates a rounded edge 16 in the first portion 12 of body 10 for the comfort of the user. The body 10 may be made of any type of relatively rigid material, such as plastic, metal, wood, etc. and may be formed by any convenient method, such as machining, injection molding, extrusions, etc. to provide the desired configuration.

Figure 2:
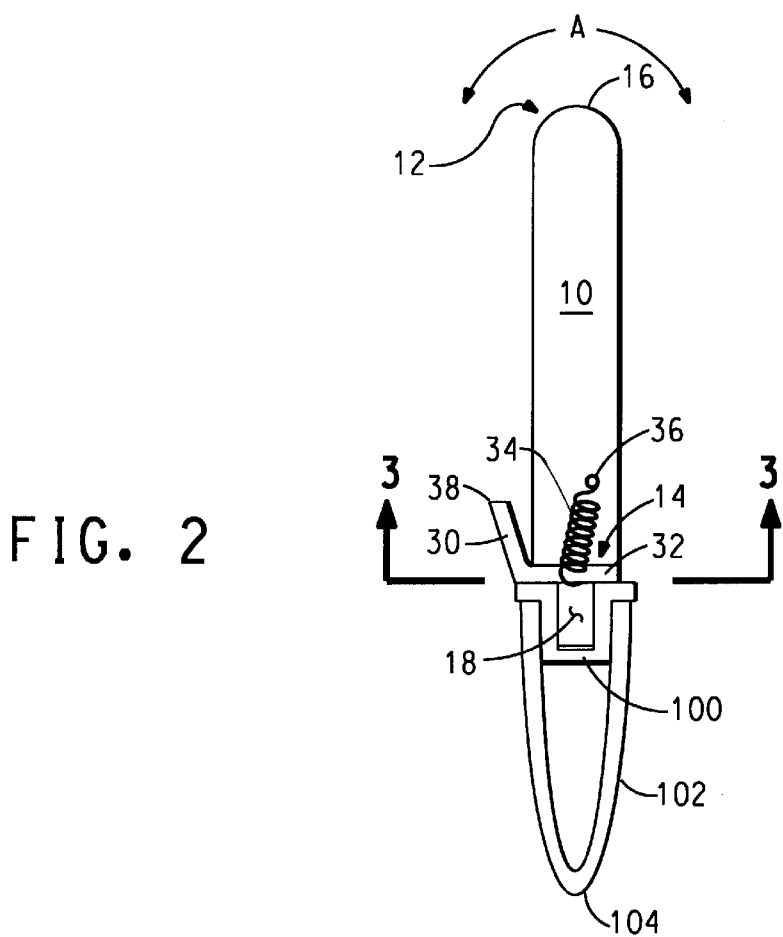
FIG. 2 is a side elevation view of the tool of the invention as seen along lines and arrows 2—2 of FIG. 1, particularly illustrating the tool in operational engagement with a typical reaction/processing tube.

The second portion 14 of body 10 is provided with a row of spaced-apart pegs 18 projecting outwardly from the body 10. With reference now being made to FIG. 2, the tool of this invention, specifically the peg 18, is shown engaged with a cap 100 of a typical reaction/processing tube 102. As mentioned above, tubes 102 are generally commercially available in strips of 8 or 12 tubes connected together by webs in a linear orientation and the caps 100 are likewise available in companion strips of 8 or 12. In the view shown in FIG. 2, the strip of tubes and caps would be oriented into and out of the plane of the paper.

As seen in FIG. 2, the tube is of generally cylindrical shape with a conical lower portion 104. Cap 100 is shown with a concave or bowl-shaped configuration and the peg 18 is structured to fit closely within the recess or "bowl" in cap 100. It is to be understood that the remainder of pegs 18 are similarly engaged. As such, by applying a force to the tool in a rocking motion, as indicated by arrow A in FIG. 2, the plurality of caps 100 will be gently eased out of the tubes 102 without any violent force being generated and without spillage of the contents of the tubes.

In the preferred embodiment shown, the tool is 7.6 cm (3 inch) long by 5.1 cm (2 inches) high and is fabricated from 0.953 cm (0.375 inch) thick acrylic. The eight cylindrical pegs 18 are spaced to correspond with the respective caps 100.

The pegs 18 extend 0.635 cm (0.250 inch) from the tool body 10 and have a diameter of 0.505 cm (0.199 inch). Although not seen in the Figures, the pegs 18 are press fit into corresponding holes in tool body 10 to a depth of 0.64 cm (0.25 inch).

With further reference to FIGS. 2 and 3, the preferred embodiment of the invention includes a tool release feature to facilitate removal of the caps 100 from the corresponding pegs 18. The tool release feature comprises a bent plate 30 with fingers 32 loosely surrounding each pin 18 on three sides, as shown. Two springs 34 (see FIG. 1) connect plate 30 to bosses 36 located on opposite ends of tool body 10 and bias the plate 30 into position against second portion 14 of tool 10. Application of pressure against flange 38 will cause plate 30 to pivot relative to the tool body 10, which in turn will cause fingers 32 to move outwardly toward the ends of pegs 18, thus facilitating the removal of any caps that may be attached to pegs 18.

In addition, those skilled in the art will readily appreciate that the tool can also be used to replace, or seat, a strip of caps 100 simply be inserting the pegs 18 into the strip of caps, aligning the caps with the tubes 102 and applying pressure to the tool.

What is claimed is:

1. A tool for use in uncapping a plurality of linearly-oriented, spaced-apart tubes, each tube having a cap having an inwardly extending hollow, said caps being in locked engagement with said tubes, the tool comprising:

a body having a first portion for engagement by a user and a second portion in a coplanar relationship with said first portion adapted to engage the plurality of caps;

said second portion comprising a row of linearly spaced-apart pegs projecting from said body and spaced to align with said caps, said pegs structured to fit closely within the hollows of said caps; and a bent plate constrained to be in contact with said body and pivotally movable relative to said body and said plurality of pegs.

2. The tool of claim 1, wherein the second portion is straight and wherein the first portion is semi-circular.

3. The tool of claim 1 wherein the side opposite the row of pegs is rounded.

4. The tool of claim 1, wherein said body is made of a material selected from the group consisting of metal, plastic and wood.

5. The tool of claim 1, wherein said bent plate is biased toward said second portion of said body.

6. The tool of claim 5, wherein said bent plate comprises a plurality of fingers in spaced relation adapted to receive a peg therebetween.

* * * * *